US010773073B2

(12) United States Patent
Stem

(10) Patent No.: US 10,773,073 B2
(45) Date of Patent: Sep. 15, 2020

(54) METHODS, IMPLANTABLE MEDICAL LEADS, AND RELATED SYSTEMS TO MONITOR AND LIMIT TEMPERATURE CHANGES IN PROXIMTY TO ELECTRODES

(71) Applicant: MEDTRONIC, INC., Minneapolis, MN (US)

(72) Inventor: Bryan D. Stem, Minneapolis, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 614 days.

(21) Appl. No.: 14/993,032

(22) Filed: Jan. 11, 2016

(65) Prior Publication Data

US 2016/0199639 A1 Jul. 14, 2016

Related U.S. Application Data

(60) Provisional application No. 62/102,510, filed on Jan. 12, 2015.

(51) Int. Cl.
*A61N 1/08* (2006.01)
*A61N 1/05* (2006.01)
(Continued)

(52) U.S. Cl.
CPC .......... *A61N 1/05* (2013.01); *A61N 1/08* (2013.01); *A61N 1/3718* (2013.01); *A61N 1/086* (2017.08); *A61N 1/36142* (2013.01)

(58) Field of Classification Search
None
See application file for complete search history.

(56) References Cited

U.S. PATENT DOCUMENTS 4,527,217 A * 7/1985 Muller-Girard ..... H01R 13/703
200/51 R
4,612,940 A * 9/1986 Kasevich ............... A61B 18/18
219/712

(Continued)

FOREIGN PATENT DOCUMENTS

DE 19738543 12/1998
WO 2011136826 A1 11/2011

OTHER PUBLICATIONS

Angelone, L.M. et al., "On the Effect of Resistive EEG Electrodes and Leads During 7 T MRI: Simulation and Temperature Measurements Studies", Elsevier, Inc., Magnetic Resonance Imaging 24, p. 801-812, 2006.

(Continued)

*Primary Examiner* — Erica S Lee
(74) *Attorney, Agent, or Firm* — Withers & Keys, LLC

(57) ABSTRACT

A temperature sensor is included within a lead in proximity to distal electrodes. The temperature sensor measures temperature change at the electrode to tissue interface. Actions can be taken when the temperature exceeds a threshold due to heating from current induced by radio frequency energy from an MRI scan. The actions may include sending a signal via telemetry from the implanted device to an external device to produce an alarm to alert an MRI technician or to instruct the MRI scanner to alter the MRI scan. The actions may include activating a switch in the conduction path of an implanted lead to block some of the RF energy and/or to activate a shunt in the conduction path to divert some of the RF energy. The temperature sensor may be of various forms and may be mounted in various locations within the lead.

24 Claims, 12 Drawing Sheets

(51) Int. Cl.
*A61N 1/37* (2006.01)
*A61N 1/36* (2006.01)

(56) References Cited

U.S. PATENT DOCUMENTS

| | | | |
|---|---|---|---|
| 5,730,134 | A | 3/1998 | Dumoulin et al. |
| 7,285,118 | B1* | 10/2007 | Lozano .............. A61B 18/1492 |
| | | | 128/898 |
| 8,200,334 | B1 | 6/2012 | Min et al. |
| 8,388,670 | B1 | 3/2013 | Zou et al. |
| 8,678,642 | B2 | 3/2014 | Jester et al. |
| 2006/0025820 | A1 | 2/2006 | Phillips |
| 2010/0274115 | A1* | 10/2010 | Werder ................ A61B 5/0031 |
| | | | 600/378 |
| 2011/0066028 | A1* | 3/2011 | Min ........................ A61B 5/01 |
| | | | 600/412 |
| 2011/0270362 | A1 | 11/2011 | Goedeke |
| 2013/0261620 | A1* | 10/2013 | Brannan .................. A61B 5/01 |
| | | | 606/41 |
| 2014/0330357 | A1* | 11/2014 | Stevenson .............. A61N 1/025 |
| | | | 607/116 |
| 2016/0199639 | A1 | 7/2016 | Stem |

OTHER PUBLICATIONS

PCT/US2016/012916, Search Report and Written Opinion, dated Apr. 21, 2016.
PCT Application No. PCT/US2016/012916 International Search Report and Written Opinion, dated Jul. 18, 2017.
PCT/US2018/039786 International Search Report and Written Opinion, dated Oct. 8, 2018.

* cited by examiner

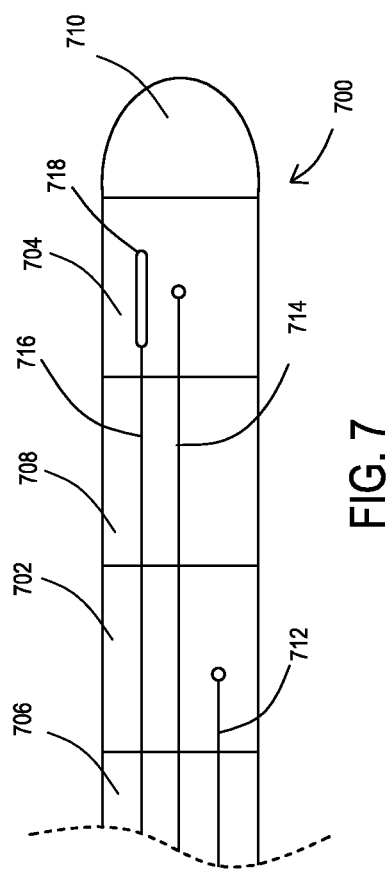
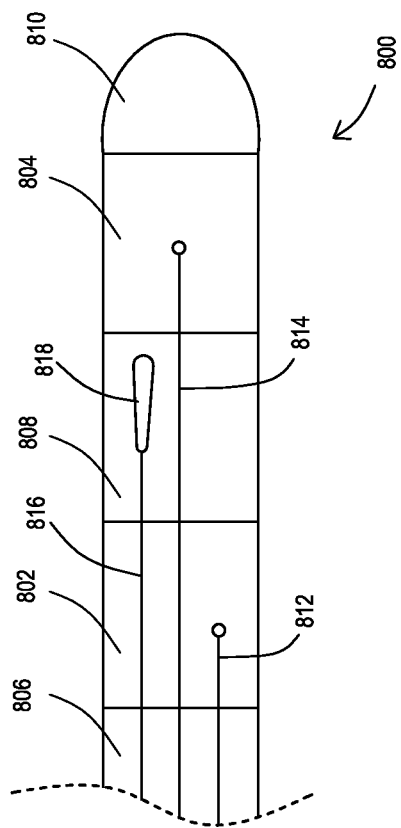
FIG. 7
FIG. 8

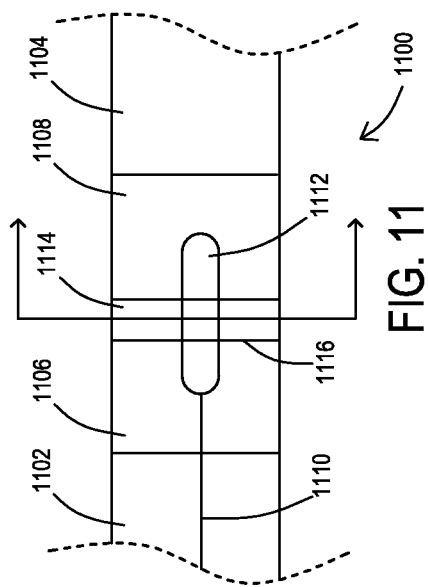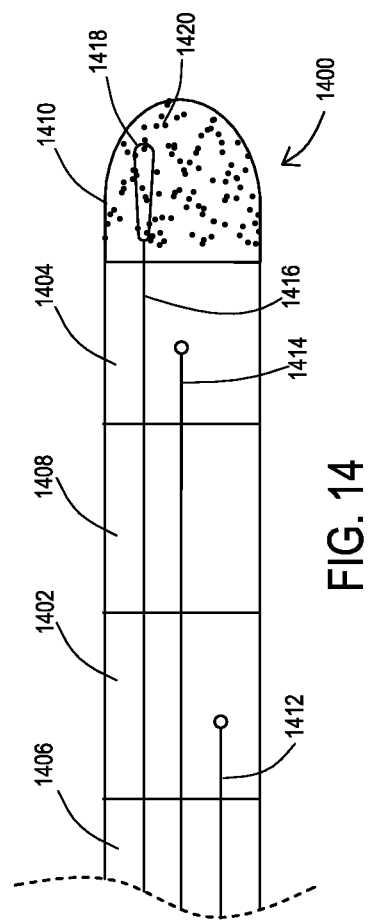

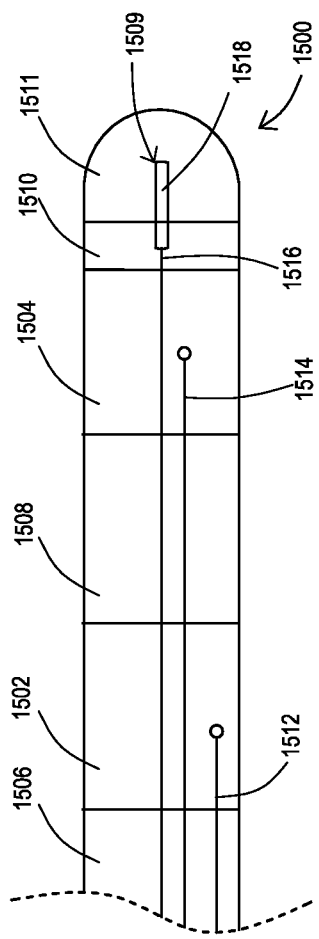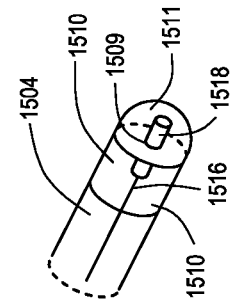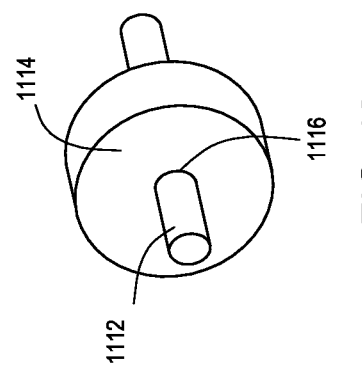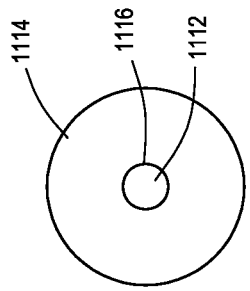

METHODS, IMPLANTABLE MEDICAL LEADS, AND RELATED SYSTEMS TO MONITOR AND LIMIT TEMPERATURE CHANGES IN PROXIMTY TO ELECTRODES

RELATED APPLICATIONS

The present application claims priority to U.S. Provisional Appl. No. 62/102,510, filed Jan. 12, 2015, and entitled METHODS, IMPLANTABLE MEDICAL LEADS, AND RELATED SYSTEMS TO MONITOR AND LIMIT TEMPERATURE CHANGES IN PROXIMTY TO ELECTRODES, which is incorporated herein by reference.

TECHNICAL FIELD

Embodiments relate to implantable medical leads and systems. More particularly, embodiments relate to implantable medical leads and systems where a temperature change in proximity to an electrode is being monitored so that the temperature change at the electrode may be limited when necessary.

BACKGROUND

Implantable medical leads include electrodes at a distal end in order to provide electrical stimulation to tissue at a target site within the body and/or to provide sensing of physiological signals at the target site. The implantable medical leads have a proximal end that is coupled to an implantable medical device (IMD) that performs the electrical stimulation and/or physiological sensing. Electrical conductors extend through the implantable medical leads from the IMD, which is positioned at a convenient implantation site, to the electrodes located at the target site.

During procedures such as a magnetic resonance imaging (MRI) scan where a level of radio frequency electromagnetic energy much greater than in normal ambient conditions is present, an electrical current is induced onto the electrical conductors of the lead. This electrical current passes through the electrode to generate heating of the electrode to tissue interface, and this heating can be potentially dangerous to the patient having the implantable medical system that includes the IMD and one or more leads. Various techniques may be used to reduce the degree of heating. One example is to include a shield within the lead that surrounds the electrical conductors. Other examples include increasing the impedance of the electrical conductors via chokes and the like.

These techniques have been proven effective for implantable medical systems where the lead is routed well below the surface of the body of the patient. However, in some cases, the lead may be routed near the surface, such as for peripheral nerve stimulation therapy. In such a case, the shallow depth of the lead within the body results in exposure to higher levels of the RF energy. These higher levels may exceed the capabilities of a lead to prevent excessive heating at the electrode to tissue interface for a lead designed originally to lessen the effects of RF energy for a deeper type of implantation.

SUMMARY

Embodiments address issues such as these and others by providing for monitoring of temperature changes within an implantable medical lead nearby an electrode in order to limit the degree of heating. A temperature sensor may be positioned within the lead and in proximity to the electrode and may have a signal path back to a temperature probe processor. When the monitored temperature as determined by the temperature probe processor exceeds a threshold, an action may be taken to limit the degree of heating. For instance, the implantable medical device or separate probe processing device may trigger an alarm via telemetry that alerts an MRI technician to stop the MRI scan or may submit a machine instruction via telemetry that stops the MRI scan. The implantable medical device may also trigger a series switch in the conduction path to open to attempt to block conduction of the RF energy and/or may trigger a shunt in parallel to the conduction path to become active to divert some of the RF energy away from the electrode being heated.

Embodiments provide a method of reducing heating at an electrode of an implantable medical system during an MRI scan. The method involves monitoring a temperature at the electrode during an MRI scan and upon detecting that the temperature being monitored exceeds a threshold, then reducing the current reaching the electrode.

Embodiments provide an implantable medical lead that includes a lead body and an electrical conductor within the lead body. The lead further includes an electrode on a distal end of the lead body and electrically coupled to the electrical conductor and includes a temperature sensor within the lead body adjacent to the electrode, the temperature sensor having a signal path within the lead body.

Embodiments provide an implantable medical system that includes an implantable medical device. The implantable medical device includes a stimulation engine and an electrical connector that is electrically coupled to an output of the stimulation engine. The implantable medical system further includes an implantable medical lead. The implantable medical lead includes a lead body, a proximal contact on a proximal end of the lead body, the proximal contact being electrically coupled to the electrical connector, and a distal electrode on a distal end of the lead body. The implantable medical lead further includes an electrical conductor that electrically interconnects the proximal contact to the distal electrode, with the proximal contact electrically coupled to the electrical connector. Additionally, the implantable medical lead includes a temperature sensor within the lead body and adjacent to the distal electrode and a signal path extending proximally from the temperature sensor through the lead body.

DESCRIPTION OF THE DRAWINGS

FIG. 7 shows an embodiment of a distal end of the lead where a temperature sensor is positioned within a distal electrode.

FIG. 8 shows an embodiment of a distal end of the lead where a temperature sensor is positioned longitudinally adjacent to a distal electrode.

FIG. 11 shows an embodiment of a distal end of the lead where a temperature sensor is positioned longitudinally adjacent to a distal electrode and within a separate conductive ring.

FIG. 12 shows a lateral cross-sectional view of the temperature sensor within the separate ring.

FIG. 13 shows a perspective view of the embodiment of FIG. 12 with the temperature sensor within the separate ring.

FIG. 14 shows an embodiment of a distal end of the lead where a temperature sensor is positioned longitudinally adjacent to a distal electrode and within a conductive filler material at the tip of the lead.

FIG. 15 shows an embodiment of a distal end of the lead where a temperature sensor is positioned longitudinally adjacent to a distal electrode and within a metal tip of the lead.

FIG. 16 shows a perspective view of the embodiment of FIG. 15 with the temperature sensor positioned within the metal tip.

DETAILED DESCRIPTION

Embodiments provide for temperature monitoring at an electrode of an implantable medical lead to allow detection of excessive heating and to further allow for action to be taken to limit further heating. The temperature sensor is positioned within the lead either within or adjacent to an electrode. A signal path for the temperature sensor may be of various forms such as an electrical conductor or a fiber optic cable. The signal path may lead to a connection within a header of an IMD or may lead to a separate probe processing unit, and the probe processing unit may be attached to either the IMD or to the lead.

Figure 1:
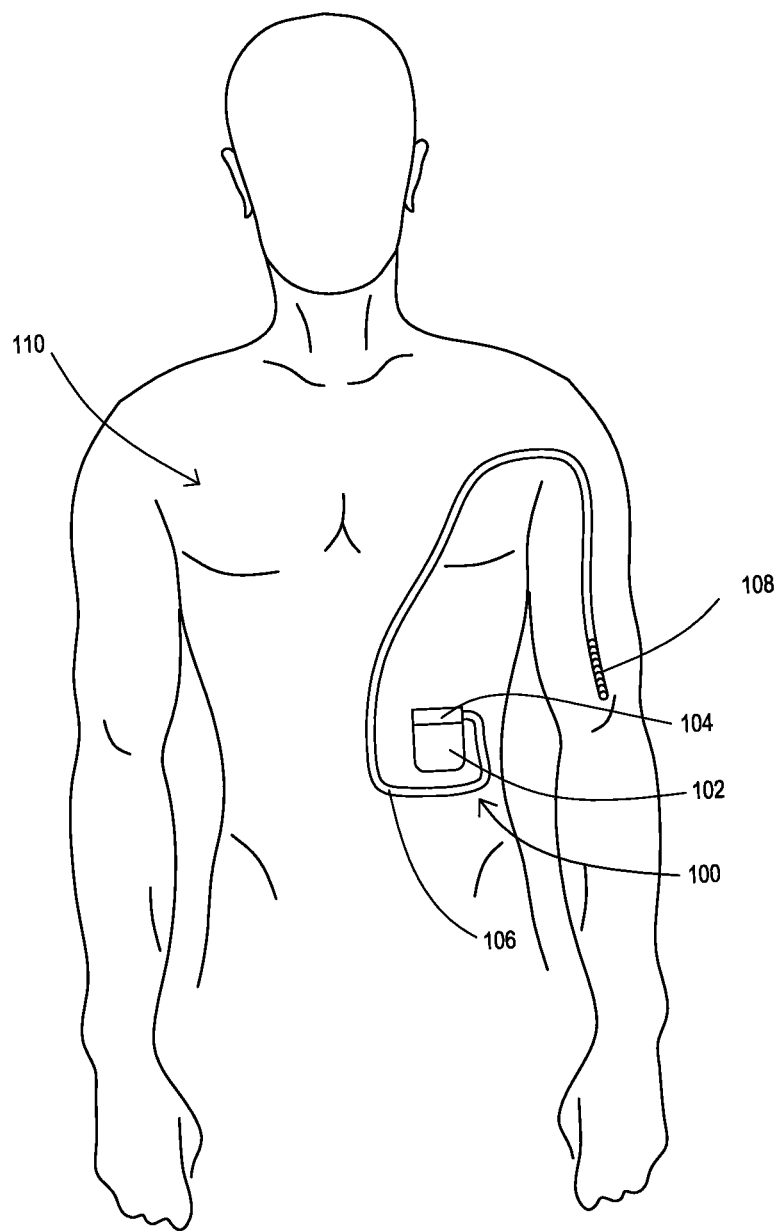
FIG. 1 shows an operating environment for various embodiments of an implantable medical system.

FIG. 1 shows an example of an implantable medical system 100 that includes an IMD 102 with a header 104 and a lead 106 coupled to the header 104 of the IMD 102. Electrodes 108 are positioned at a distal end of the lead 106 and are located at a target site within the body of a patient 110. In this example, the target site is within the arm of the patient 110 to provide peripheral nerve stimulation, but it will be appreciated that the target site may be located in other areas of the body of the patient 110.

Figure 2:
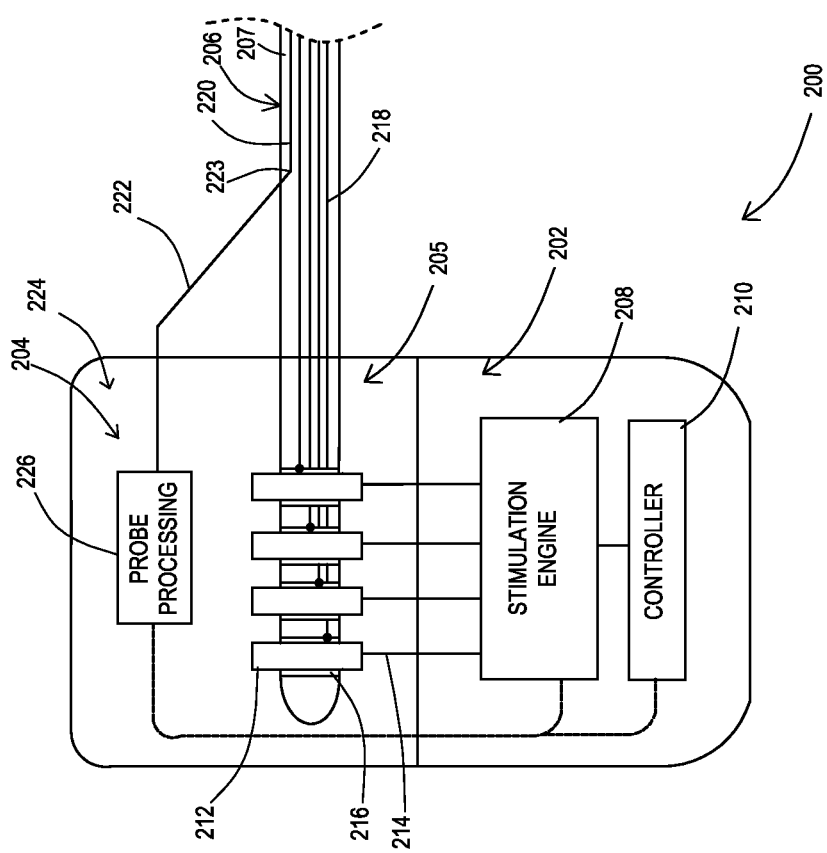
FIG. 2 shows an embodiment of an implantable medical device and an implantable medical lead coupled together and providing a fiber optic cable as a signal path for a temperature sensor.

FIG. 2 shows an embodiment of an implantable medical system 200 where an IMD 202 includes a header portion 204 that includes a first bore 205 where a proximal end of a lead 206 is inserted. The header portion 204 also includes a second bore 224 where a proximal portion 222 of a fiber optic cable is inserted. The proximal portion 222 exits from a body 207 of the lead 206 at an exit point 223. The remaining portion 220 extends distally through the body 207 of the lead 206 to the temperature sensor (not shown in this view).

The proximal portion 222 engages a port of a probe processing unit 226 that is positioned within the header portion 204. The probe processing unit 226 may be a conventional temperature sensing unit with a fiber optic port suitable for receiving the fiber optic cable portion 222. The probe processing unit 226 may have an output that is electrically coupled to a stimulation engine 208 and/or to a controller 210 of the IMD 202. The probe processing unit 226 may then output a signal representative of the measured temperature to a controller 210, and the controller 210 may then compare the temperature to a threshold and take further action. For instance, the controller 210 may cause the stimulation engine 208 or other circuit to operate a switch to shunt energy to the device casing or other heat sink or to operate a switch near the electrodes to open the circuit or shunt the energy elsewhere. The controller may additionally or alternatively telemeter an alarm or machine instruction to an external device to cause the MRI scan to be altered. The controller 210 has telemetry circuitry either integral or coupled thereto which allows communication with external devices. Alternatively, the probe processing unit may perform additional logic such as comparing the temperature to a threshold and then sending an interrupt signal to the stimulation engine 208 or other circuit to cause further action to be taken such as shunting away the energy to the casing or a heat sink.

The lead 206 also includes one or more electrical conductors 218 that lead to one or more corresponding electrodes on the distal end (not shown in this view) and to one or more corresponding electrical contacts 216 on the proximal end. The header portion 204 includes conventional electrical connectors 212 that are electrically connected via feed through conductors 214 passing from the header portion 204 through a conventional feed through hermetic seal to the stimulation engine 208.

Figure 3:
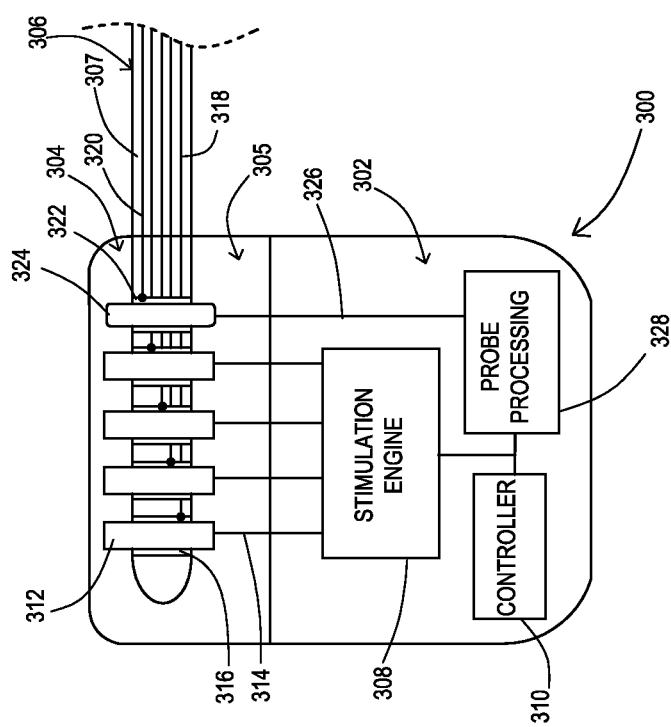
FIG. 3 shows an embodiment of an implantable medical device and an implantable medical lead coupled together and providing an electrical conductor and header connection as a signal path for a temperature sensor.

FIG. 3 shows an embodiment of an implantable medical system 300 where an IMD 302 includes a header portion 304 that includes a first bore 305 where a proximal end of a lead 306 is inserted. The proximal end includes an electrical contact 322 that is dedicated to temperature sensor signals and couples to a dedicated electrical connector 324 of the header portion 304. An electrical conductor 320 that is dedicated to the temperature sensor located at the distal end of the lead (not shown in this view) passes through the lead body 307 and is electrically coupled to the dedicated electrical contact 322. Likewise, an electrical feedthrough conductor 326 passes the electrical signal of the temperature sensor from the electrical connector 324 through a conventional feedthrough hermetic seal to a probe processing unit 328 within the IMD 302.

As with FIG. 2, the probe processing unit 328 may be a conventional temperature sensing unit but in this case has an electrical connection suitable for receiving the electrical signals produced by the temperature sensor connected to the electrical conductor 320. The probe processing unit 328 may have an output that is electrically coupled to a stimulation engine 308 and/or to a controller 310 of the IMD 302. The probe processing unit 328 may then output a signal representative of the measured temperature to the controller 310, and the controller 310 may then compare the temperature to a threshold and take further action such as causing the stimulation engine 308 or other circuit to operate a switch to shunt energy to the device casing or other heat sink or to operate a switch near the electrodes to open the circuit or shunt the energy elsewhere or to telemeter an alarm or machine instruction to an external device to cause the MRI scan to be altered. Alternatively, the probe processing unit 328 may perform additional logic such as comparing the temperature to a threshold and then sending an interrupt signal to the stimulation engine 308 or other circuit to cause further action to be taken such as shunting the energy away.

The lead 306 also includes one or more electrical conductors 318 that lead to one or more corresponding electrodes on the distal end (not shown in this view) and to one or more corresponding electrical contacts 316 on the proximal end. The header portion 304 includes conventional electrical connectors 312 that are electrically connected via feed through conductors 314 passing from the header portion 304 through a conventional feed through hermetic seal to the stimulation engine 308.

Figure 4:
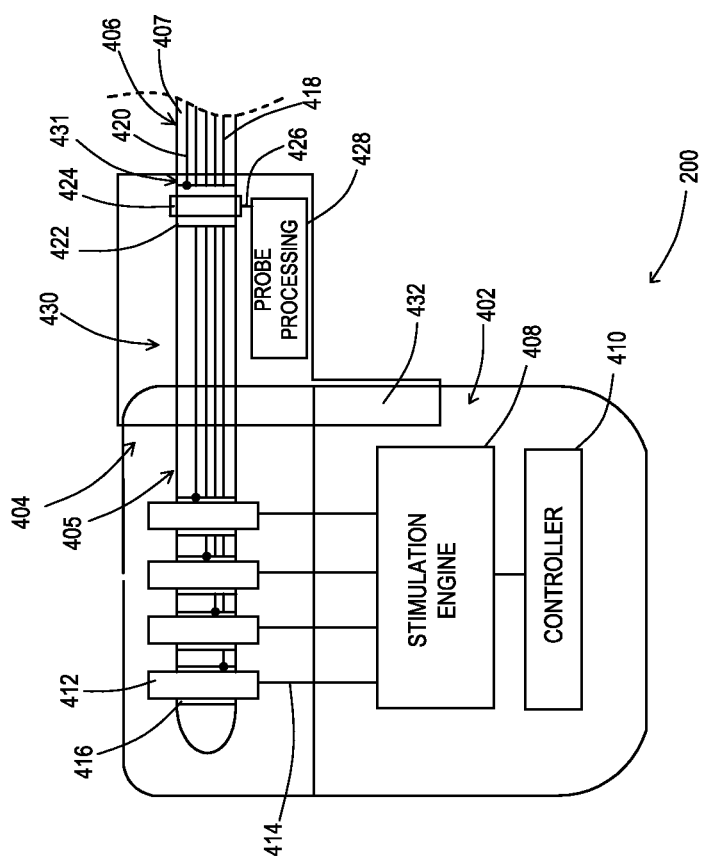
FIG. 4 shows an embodiment of an implantable medical device and an implantable medical lead coupled together and providing a signal path for a temperature sensor that terminates to a separate probe processing unit attached to the implantable medical device.
Figure 6:
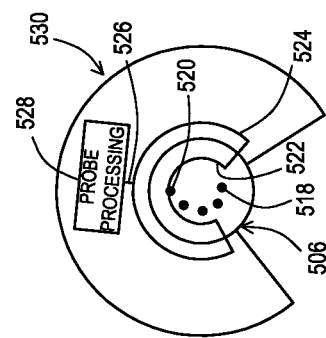
FIG. 6 shows a lateral cross-sectional view of the separate probe processing unit and lead of the embodiment of FIG. 5.

FIG. 4 shows an embodiment of an implantable medical system 400 where a separate probe processing enclosure 430 is attached to the IMD 402. The probe processing enclosure 430 may include various mounting structures 432 such as a flange that compresses against the IMD 402 to fix the enclosure 430 in place. The enclosure 430 includes a bore 431 where a proximal end of an implantable medical lead 406 passes entirely through the enclosure 430 in order to enter a bore 405 of a header portion 404 of the IMD 402.

In this example, the lead 406 includes an electrical contact 422 that is electrically coupled to a dedicated electrical conductor 420 within a lead body 407 of the lead 406. The electrical conductor 420 extends distally to a temperature sensor at a distal end of the lead 406 (not shown in this view). The electrical contact 422 electrically couples to an electrical connector 424 within the bore 431 of the enclosure 430.

A probe processing unit 428 is within the enclosure 430 and therefore separate from the IMD 402. In this example, an electrical conductor 426 electrically couples the probe processing unit 428 to the electrical connector 424. The conductor 426 may pass the electrical signal of the temperature sensor from the electrical connector 424 through a conventional feedthrough hermetic seal of the enclosure 430 to the probe processing unit 428.

While this example shows an electrical conductor 420 and an electrical signal path to the probe processing unit 428, it will be appreciated that a fiber cable could be used with the enclosure 430 and separate probe processing unit. For example, a fiber optic cable within the lead body 407 may exit the lead body distally of the enclosure 430 and then be received within a bore of the enclosure 430, in a similar fashion to the manner in which the header portion 204 receives the fiber cable portion 222 in a bore 205 in FIG. 2.

As with the prior examples, the probe processing unit 428 may be a conventional temperature sensing unit. The probe processing unit 428 may either be configured to receive an electrical signal via the conductor 426 or receive a fiber cable in the alternative. The probe processing unit 428 may have a telemetry circuit to allow the probe processing unit 428 to provide the temperature information to the controller 210. Alternatively, the probe processing unit 428 may perform additional logic such as comparing the temperature to a threshold and then triggering a switch to trigger to shunt the energy away.

The lead 406 also includes one or more electrical conductors 418 that lead to one or more corresponding electrodes on the distal end (not shown in this view) and to one or more corresponding electrical contacts 416 on the proximal end. The header portion 404 includes conventional electrical connectors 412 that are electrically connected via feed through conductors 414 passing from the header portion 404 through a conventional feed through hermetic seal to the stimulation engine 408 which is being controlled by a controller 410.

Figure 5:
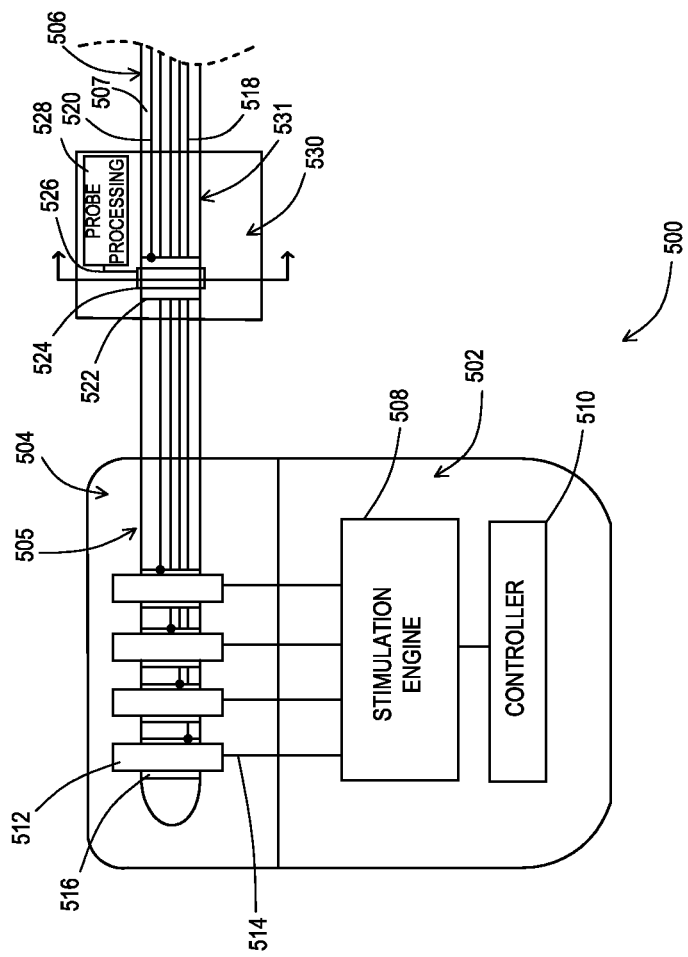
FIG. 5 shows an embodiment of an implantable medical device and an implantable medical lead coupled together and providing a signal path for a temperature sensor that terminates to a separate probe processing unit attached to the implantable medical lead.

FIG. 5 shows an embodiment of an implantable medical system 500 where a separate probe processing enclosure 530 is attached to a lead 506. The probe processing enclosure 530 may include mounting structures such as an interference fit as shown in the lateral cross-sectional view of FIG. 5 that compresses against the lead 506 to fix the enclosure 530 in place. The enclosure 530 includes a bore 531 where a proximal end of the implantable medical lead 506 passes entirely through the enclosure 530 in order to enter a bore 505 of a header portion 504 of the IMD 502.

In this example, the lead 506 includes an electrical contact 522 that is electrically coupled to a dedicated electrical conductor 520 within a lead body 507 of the lead 506. The electrical conductor 520 extends distally to a temperature sensor at a distal end of the lead 506 (not shown in this view). The electrical contact 522 electrically couples to an electrical connector 524 within the bore 531 of the enclosure 530.

A probe processing unit 528 is within the enclosure 530 and therefore separate from the IMD 502. In this example, an electrical conductor 526 electrically couples the probe processing unit 528 to the electrical connector 524. The conductor 526 may pass the electrical signal of the temperature sensor from the electrical connector 524 through a conventional feedthrough hermetic seal of the enclosure 530 to the probe processing unit 528.

While this example shows an electrical conductor 520 and an electrical signal path to the probe processing unit 528, it will be appreciated that a fiber cable could be used with the enclosure 530 and separate probe processing unit. For example, a fiber optic cable within the lead body 507 may exit the lead body distally of the enclosure 530 and then be received within a bore of the enclosure 530, in a similar fashion to the manner in which the header portion 204 receives the fiber cable portion 222 in a bore 205 in FIG. 2.

As with the prior examples, the probe processing unit 528 may be a conventional temperature sensing unit. The probe processing unit 528 may either be configured to receive an electrical signal via the conductor 526 or receive a fiber cable in the alternative. The probe processing unit 528 may have telemetry to communicate with the controller as described above for the probe processing unit of FIG. 4. Alternatively, the probe processing unit 528 may perform additional logic such as comparing the temperature to a threshold and then trigger a switch to shunt the energy away.

The lead 506 also includes one or more electrical conductors 518 that lead to one or more corresponding electrodes on the distal end (not shown in this view) and to one or more corresponding electrical contacts 516 on the proximal end. The header portion 504 includes conventional electrical connectors 512 that are electrically connected via feed through conductors 514 passing from the header portion 504 through a conventional feed through hermetic seal to the stimulation engine 508 which is being controlled by a controller 510.

For each of the examples discussed above where an electrical signal is being generated by the temperature sensor, if two conduction paths back to the probe processing unit are required, then the conductor in the lead body may be two separately insulated conductors and that terminate in two separate electrical contacts on the lead. The probe processing unit may then be coupled to two separate electrical connectors that electrically couple to the two separate electrical contacts. As an alternative, one of the conduction paths may be through the body tissue of the patient where the probe processing unit is coupled to a conductive encasement that contacts the body tissue to complete the conduction path to the probe processing unit. FIG. 7 shows an example of a distal end of a lead 700 which may be used with the various embodiments discussed above in relation to FIGS. 1-6. In this example, the lead 700 includes a lead body 706 having an electrode 702 separated by an insulator region 708 from another electrode 704. An electrical conductor 712 is coupled to the electrode 702 and extends proximally back to a proximal end contact as discussed above in relation to the proximal end of the lead examples. Likewise, an electrical conductor 714 is coupled to the electrode 704 and extends proximally back to a proximal end contact. An insulative tip section 710 may be included distally of the electrode 704.

A temperature sensor 718 may be included within one of the electrodes as shown. The temperature sensor 718 may be of various conventional forms such as a thermocouple with an electrical or optical output. A temperature sensor 718 having an electrical output may require a two conductor path back to the probe processing unit and in such a case, multiple insulated conductors may be present within the signal path 716 and multiple electrical contacts may be present on the lead and in the header or separate enclosure at the proximal end to receive the two conduction paths. As another example, the conduction of the body tissue may be utilized as one of the conduction paths.

FIG. 8 shows another example of a distal end of a lead 800 which may be used with the various embodiments discussed above in relation to FIGS. 1-6. In this example, the lead 800 includes a lead body 806 having an electrode 802 separated by an insulator region 808 from another electrode 804. An electrical conductor 812 is coupled to the electrode 802 and extends proximally back to a proximal end contact as discussed above in relation to the proximal end of the lead examples. Likewise, an electrical conductor 814 is coupled to the electrode 804 and extends proximally back to a proximal end contact. An insulative tip section 810 may be included distally of the electrode 804.

A temperature sensor 818 may be included within the insulative region 808 adjacent to the electrodes 802, 804 as shown. The temperature sensor 818 may be of various conventional forms as discussed above in relation to FIG. 7. As discussed above, the temperature sensor 818 having an electrical output may require a two conductor path back to the probe processing unit and in such a case, multiple insulated conductors may be present within the signal path 816 and multiple electrical contacts may be present on the lead and in the header or separate enclosure at the proximal end to receive the two conduction paths. As another example, the conduction of the body tissue may be utilized as one of the conduction paths.

Figure 9:
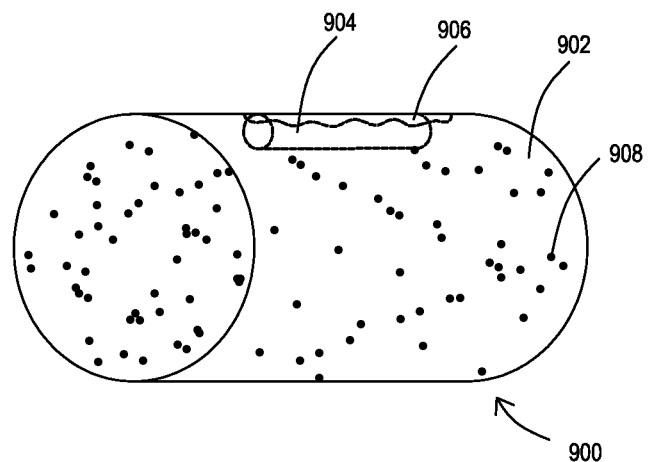
FIG. 9 shows an embodiment where the temperature sensor is affixed to an interior surface of an electrode.

FIG. 9 shows an example 900 of mounting a temperature sensor 904 within an electrode 902 which has the form of a ring. The temperature sensor 904 may be attached to an inside surface of the electrode 902. A medical adhesive 906 may be applied to fix the temperature sensor 904 in position. Furthermore, a conductive epoxy 908 may backfilled within the electrode around the temperature sensor 904.

Figure 10:
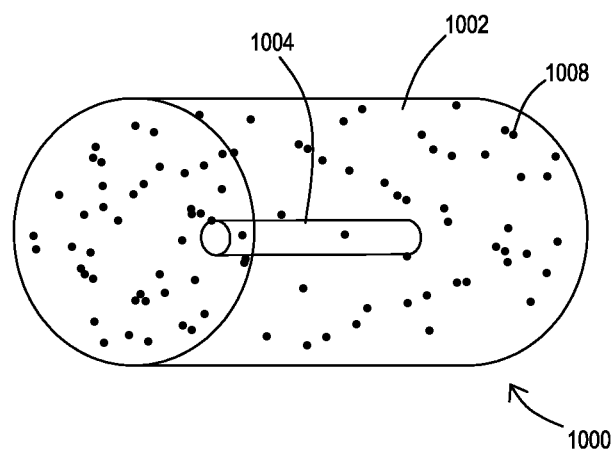
FIG. 10 shows an embodiment where the temperature sensor is encapsulated in a conductive filler material that may be positioned within an electrode or elsewhere within the lead.

FIG. 10 shows an example 1000 where a temperature sensor 1004 is suspended within a conductive epoxy filler 1008. The filler 1008 forms a cylinder 1002 that may fit within the insulative region of the lead body between electrodes or within one of the electrodes.

FIG. 11 shows an alternative configuration for including a temperature sensor 1112 adjacent to an electrode 1104. In this example the temperature sensor 1112 is located between an electrode 1102 and the electrode 1104 and is positioned within an aperture 1116 of a conductive ring 1114. This configuration of the temperature sensor 1112 and ring 1114 can be further seen in the lateral cross-sectional view of FIG. 12 and the perspective view of FIG. 13. The conductive ring 1114 is present between insulative portions 1106 and 1108 of the lead 1100 and holds the temperature sensor 1112 in a fixed position. The conductive ring 1114 may be encapsulated within the lead body or may be exposed to the tissue of the patient. The temperature sensor 1112 provides a signal over the signal path 1110 that extends proximally to the proximal end of the lead.

FIG. 14 shows another example of a distal end of a lead 1400 that has electrodes 1402 and 1404 attached to a lead body 1406 and electrical conductors 1412 and 1414 attached to the respective electrodes 1402, 1404. An insulative region 1408 is present between the electrodes 1402, 1404. In this example, the temperature sensor 1418 is located within a tip 1410 of the lead 1400. The tip 1410 may be constructed of an insulative material and then backfilled with a conductive filler material 1420 to fix the temperature sensor 1418 within the tip 1410. The temperature sensor 1418 provides a signal over the signal path 1416 that extends proximally to the proximal end of the lead 1400.

FIG. 15 shows another example of a distal end of a lead 1500 that has electrodes 1502 and 1504 attached to a lead body 1506 and electrical conductors 1512 and 1514 attached to the respective electrodes 1502, 1504. An insulative region 1508 is present between the electrodes 1502, 1504. In this example, the temperature sensor 1518 is located within a tip 1511 of the lead 1500. The tip 1511 is constructed of metal and includes a bore 1509 that the temperature sensor 1518 is tightly positioned within to fix the position of the temperature sensor 1518 within the tip 1511. An additional insulative portion 1510 may be present to separate the metal tip 1511 from the electrode 1504. The configuration of the temperature sensor 1518 and insulative region 1510 can be further seen in the perspective view of FIG. 16. The temperature sensor 1518 provides a signal over the signal path 1516 that extends proximally to the proximal end of the lead 1500.

Figure 17:
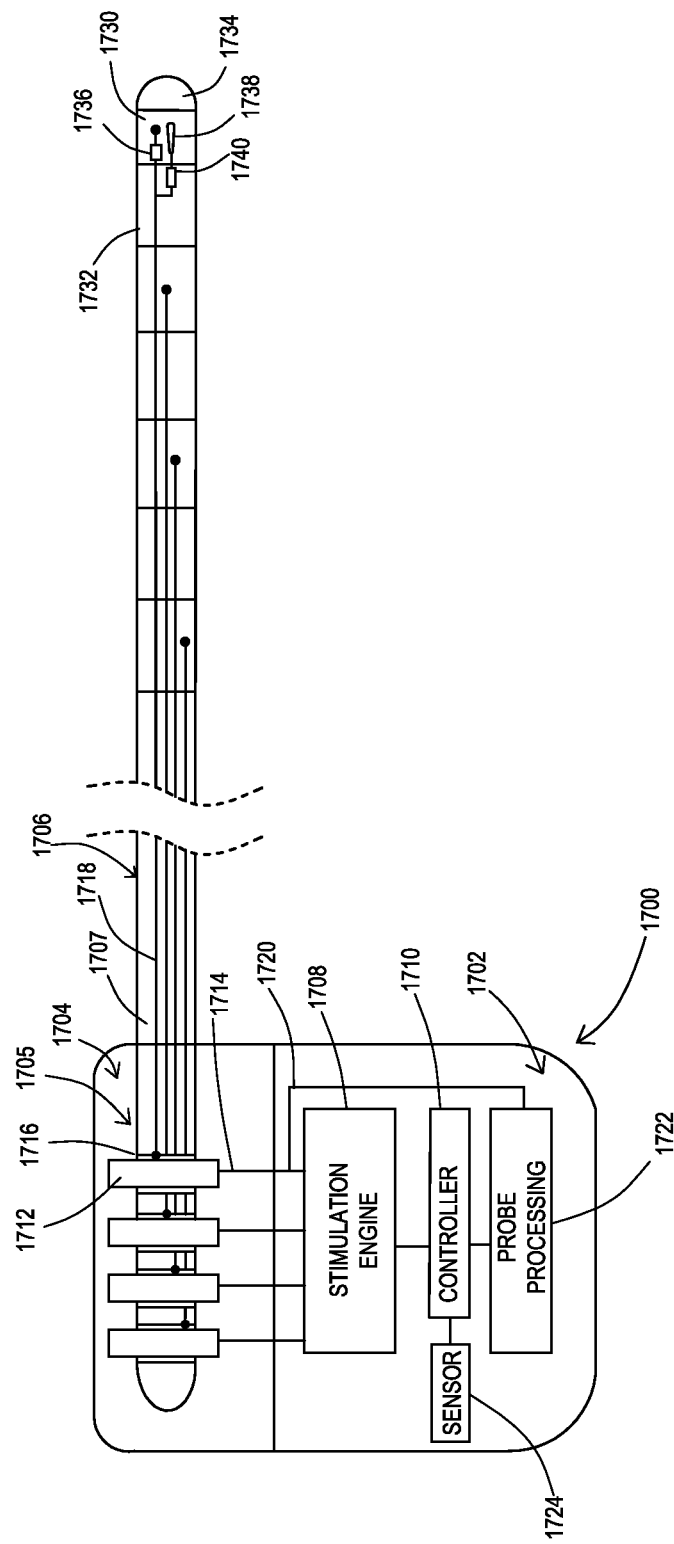
FIG. 17 shows an embodiment of an implantable medical system where the signal path for the temperature sensor is an electrical conductor that is also coupled to the electrode.

FIG. 17 an embodiment of an implantable medical system 1700 where an IMD 1702 includes a header portion 1704 that includes a first bore 1705 where a proximal end of a lead 1706 is inserted. The proximal end includes an electrical contact 1716 that provides the multiple functions of carrying stimulation or physiological sensing signals and also carrying temperature sensor signals. The electrical contact 1716 couples to an electrical connector 1712 of the header portion 1704. An electrical conductor 1718 that passes through the lead body 1707 to a temperature sensor 1738 and to an electrode 1730 and is electrically coupled to the electrical contact 1716. Likewise, an electrical feedthrough conductor 1714 passes the stimulation signals and electrical signals of the temperature sensor 1738 from the electrical connector 1712 through a conventional feedthrough hermetic seal. Within the IMD 1702, the signal path branches to both a stimulation engine 1708 though portion 1721 and to a probe processing unit 1722 through portion 1720.

The distal end of the lead 1706 includes a tip 1734 and one or more electrodes 1730. While this example shows the temperature sensor 1738 within the electrode 1730, it will be appreciated that any of the temperature sensor mounting methods discussed above may be utilized such as including the temperature sensor in the insulative region 1732 adjacent the electrode 1730 or within the tip 1734.

In order to isolate the temperature sensor 1738 from stimulation or sensed physiological signals during normal operation outside of an MRI scan, a magnetically sensitive switch 1740 configured to close when in the presence of a strong magnetic field from an MRI is in series with the temperature sensor 1738 to isolate the temperature sensor. Likewise, to isolate the electrode 1730 from temperature sensor signals, a second magnetically sensitive switch 1736 configured to open when in the presence of a strong magnetic field from an MRI may be in series with the electrode 1730 to isolate the electrode 1730. An example of the magnetically sensitive switch may be found in U.S. Application No. 61/981,768 which is incorporated herein by reference.

Returning to the IMD 1702, the probe processing unit 1722 may be a conventional temperature sensing unit but in this case has an electrical connection suitable for receiving the electrical signals produced by the temperature sensor 1738. The probe processing unit 1722 may have an output that is electrically coupled to the stimulation engine 1708 and/or to a controller 1710 of the IMD 1702. The probe processing unit 1722 may then output a signal representative of the measured temperature to the controller 1710, and the controller 1710 may then compare the temperature to a threshold and take further action such as causing the stimulation engine 1708 or other circuit to shunt any energy to the device case or other heat sink, or to telemeter an alarm or machine instruction to an external device to cause the MRI scan to be altered. Alternatively, the probe processing unit 1722 may perform additional logic such as comparing the temperature to a threshold and then sending an interrupt signal to the stimulation engine 1722 or other circuit to cause further action to be taken such as operating a switch to shunt the energy away.

Figure 18:
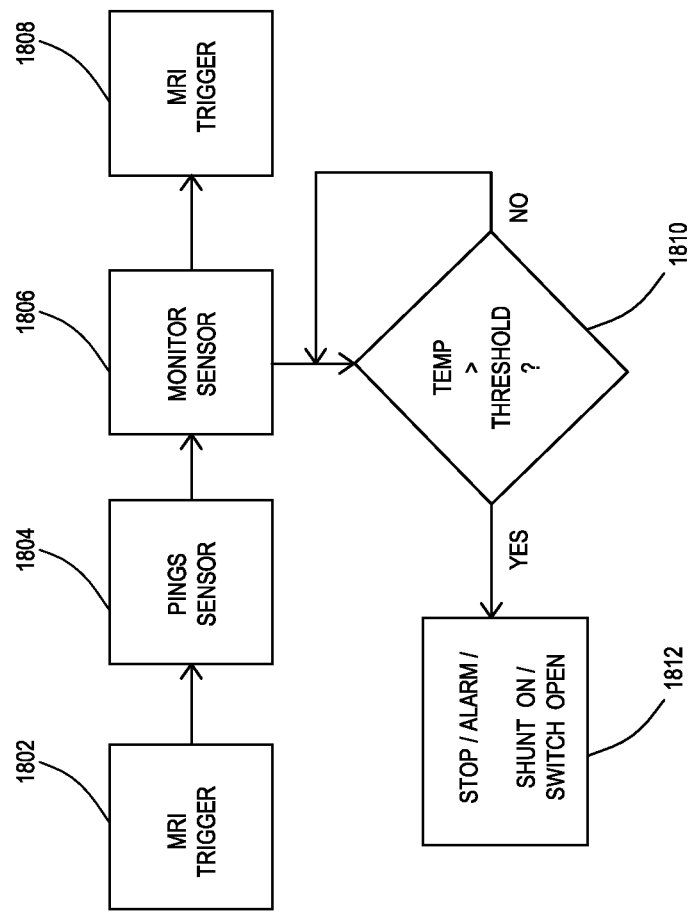
FIG. 18 shows a set of operations that an implantable medical device or separate probe processing device may perform to monitor the temperature change at the electrode and limit the temperature increase when using a fiber optic cable or electrical conductor not shared with an electrode.

FIG. 18 shows a set of operations that may be performed by a controller of an IMD as introduced for the various embodiments above where a temperature sensor with a fiber optic signal path or a dedicated electrical path is being used. In this example, the controller receives an MRI trigger at an operation 1802, such as receiving a telemetry signal that instructs the controller to enter an MRI mode of operation and/or by having a sensor like that of FIG. 17 that detects the magnetic field of the MRI. Upon receiving the MRI trigger, the controller then pings the temperature sensor by communicating with the probe processing unit of the temperature sensor to cause the probe processing unit to begin providing a temperature reading at an operation 1804. The controller continues to monitor the sensor at an operation 1806.

While monitoring the temperature readings, the controller detects whether the temperature being read exceeds a temperature threshold at a query operation 1810. This process continues until another MRI trigger is received at an operation 1808, such as receiving a telemetry signal indicating the controller should exit the MRI mode of operation or by a sensor no longer detecting the magnetic field of an MRI. If the controller detects that the temperature does exceed a threshold at the query operation 1810, then the controller initiates an action to limit any further increase in the temperature at an operation 1812.

The actions taken may be of various forms. For example, the controller may telemeter an alarm that an external device may produce to cause an MRI technician to reduce the RF power or to terminate the MRI scan. As another example, the controller may telemeter a machine instruction to the MRI scanner that causes the MRI scanner to reduce the RF power or to terminate the MRI scan. As another example, the controller may trigger a switch in series with the electrodes to transition to an open state to block some RF energy from reaching the electrodes, and/or the controller may trigger a shunt in parallel with the electrodes to become active to divert some RF energy away from the electrodes.

Figure 19:
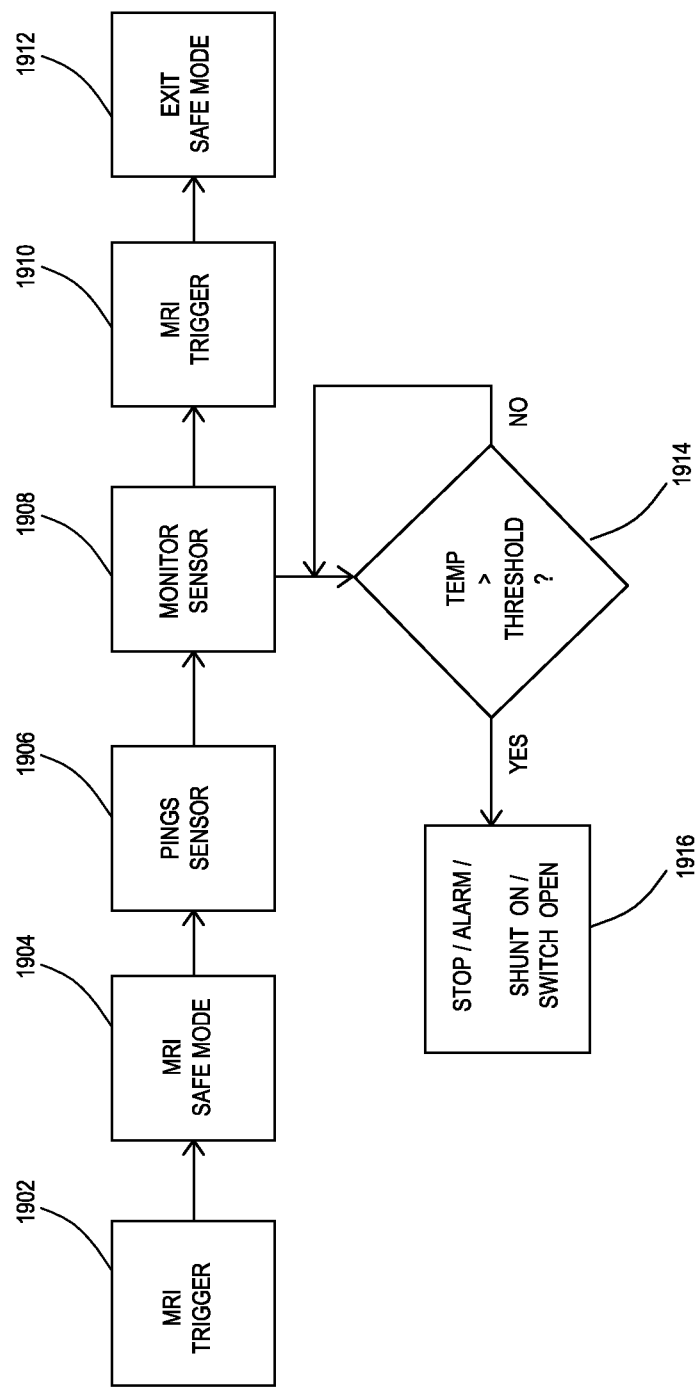
FIG. 19 shows a set of operations that an implantable medical device may perform to monitor the temperature change at the electrode and limit the temperature increase when the temperature probe shares an electrical conductor with the electrode.

FIG. 19 shows a set of operations that may be performed by a controller of an IMD as introduced for the various embodiments above where a temperature sensor shares an electrical path with an electrode. In this example, the controller receives an MRI trigger at an operation 1902, such as receiving a telemetry signal that instructs the controller to enter an MRI mode of operation and/or by having a sensor like that of FIG. 17 that detects the magnetic field of the MRI. Upon receiving the MRI trigger, the controller then enters an MRI mode of operation where the stimulation path is blocked while the temperature signal path is activated for the shared signal path at an operation 1904. The controller then pings the temperature sensor by communicating with the probe processing unit of the temperature sensor to cause the probe processing unit to begin providing a temperature reading at an operation 1906 by communicating with the temperature sensor over the shared electrical signal path. The controller continues to monitor the sensor at an operation 1908.

While monitoring the temperature readings, the controller detects whether the temperature being read exceeds a temperature threshold at a query operation 1914. This process continues until another MRI trigger is received at an operation 1910, such as receiving a telemetry signal indicating the controller should exit the MRI mode of operation or by a sensor no longer detecting the magnetic field of an MRI. The MRI mode is then exited at operation 1912 where the temperature signal path is then blocked while the stimulation signal path is activated for the shared signal path. If the controller detects that the temperature does exceed a threshold at the query operation 1914, then the controller initiates an action to limit any further increase in the temperature at an operation 1916. The actions taken may include those discussed above in FIG. 18.

Thus, by monitoring the temperature at the electrodes, it can be determined whether operation of the MRI scan may continue as currently configured or whether some action to limit the temperature increase at the electrodes is necessary. Accordingly, the temperature monitoring aids in avoiding risks associated with heating at the electrode to tissue interface due to induced RF energy.

While embodiments have been particularly shown and described, it will be understood by those skilled in the art that various other changes in the form and details may be made therein without departing from the spirit and scope of the invention.

What is claimed is:

1. An implantable medical lead, comprising:
   a lead body;

an electrical conductor within the lead body;

an electrode on a distal end of the lead body and electrically coupled to the electrical conductor; and a temperature sensor contained entirely within the lead body and adjacent the electrode, the temperature sensor having a signal path within the lead body, wherein the signal path comprises a first switch that is magnetically triggered to complete the signal path in the presence of a magnetic field.

2. The implantable medical lead of claim 1, wherein the first switch of the signal path is present within the lead body.

3. The implantable medical lead of claim 1, wherein the signal path comprises the electrical conductor and wherein the temperature sensor is electrically coupled to the electrical conductor.

4. The implantable medical lead of claim 1, further comprising a second switch in series between the electrical conductor and the electrode.

5. The implantable medical lead of claim 4, wherein the second switch is magnetically triggered.

6. An implantable medical system, comprising:
an implantable medical device that comprises:
a stimulation engine; and
an electrical connector that is electrically coupled to an output of the stimulation engine; and
an implantable medical lead that comprises:
a lead body;
a proximal contact on a proximal end of the lead body, the proximal contact being electrically coupled to the electrical connector;
a distal electrode on a distal end of the lead body;
an electrical conductor that electrically interconnects the proximal contact to the distal electrode, with the proximal contact electrically coupled to the electrical connector;
a temperature sensor surrounded by the distal electrode; and
a signal path extending proximally from the temperature sensor through the lead body, wherein the signal path comprises a first switch that is magnetically triggered to complete the signal path in the presence of a magnetic field.

7. The implantable medical system of claim 6, wherein the first switch is magnetically triggered while being present within the lead body.

8. The implantable medical system of claim 6, wherein the signal path comprises the electrical conductor and wherein the temperature sensor is electrically coupled to the electrical conductor.

9. The implantable medical system of claim 8, wherein the electrical conductor extends to a proximal contact on the lead and wherein the proximal contact resides within a bore of a header of the implantable medical device when the lead is fully inserted into the bore.

10. The implantable medical system of claim 6, further comprising a second switch in series between the electrical conductor and the electrode.

11. The implantable medical system of claim 10, wherein the second switch is magnetically triggered.

12. The implantable medical system of claim 6, wherein the signal path comprises a second electrical conductor electrically coupled to the temperature sensor and wherein the lead includes a proximal contact in electrical communication with the temperature sensor through the second electrical conductor where the proximal contact resides outside of a bore of a header of the implantable medical device when the lead is fully inserted into the bore.

13. The implantable medical system of claim 12, further comprising a probe processing unit attached to an exterior of the implantable medical device, the probe processing unit having an electrical connector electrically coupled to the proximal contact.

14. The implantable medical system of claim 12, further comprising a probe processing unit attached to an exterior of the lead, the probe processing unit having an electrical connector electrically coupled to the proximal electrical contact.

15. A method of reducing heating at a distal electrode attached to a lead body of an implantable medical system during an MM scan, comprising:
monitoring a temperature at the electrode during an MRI scan by providing a temperature sensor entirely contained inside of the lead body and adjacent the electrode, the temperature sensor having a signal path within the lead body and wherein the signal path comprises a first switch that is magnetically triggered to complete the signal path in the presence of a magnetic field, where an electrical conductor is present within the lead body and electrically coupled to the electrode; and
upon detecting that the temperature being monitored exceeds a threshold, then reducing the current reaching the electrode.

16. The method of claim 15, wherein reducing the current reaching the electrode comprises opening a second switch in series with the electrode.

17. The method of claim 15, wherein reducing the current reaching the electrode comprises activating a shunt in parallel with the electrode.

18. The method of claim 15, wherein reducing the current reaching the electrode comprises producing a signal to alter the MM scan.

19. The method of claim 18, wherein the signal to alter the MRI scan is a machine instruction to stop the MM scan.

20. The method of claim 18, wherein the signal to alter the MRI scan produces an alarm perceivable by an MM technician.

21. The method of claim 15, wherein the first switch is present within the lead body.

22. The method of claim 15, wherein including the temperature sensor comprises including an electrical connection between the temperature sensor and the electrical conductor within the lead body.

23. The method of claim 22, wherein the electrical conductor extends to a proximal contact on the lead.

24. The method of claim 23, wherein the proximal contact resides within a bore of a header of an implantable medical device when the lead is fully inserted into the bore.

* * * * *